(12) United States Patent
Weisshaupt et al.

(10) Patent No.: US 9,289,216 B2
(45) Date of Patent: Mar. 22, 2016

(54) SURGICAL CLIP

(71) Applicant: Aesculap AG, Tuttlingen (DE)

(72) Inventors: Dieter Weisshaupt, Immendingen (DE); Markus Nesper, Tuttlingen (DE); Klaus-Dieter Steinhilper, Tuttlingen (DE); Thomas Pleil, Bad Duerrheim (DE)

(73) Assignee: Aesculap AG, Tuttlingen (DE)

( * ) Notice: Subject to any disclaimer, the term of this patent is extended or adjusted under 35 U.S.C. 154(b) by 414 days.

(21) Appl. No.: 13/758,148

(22) Filed: Feb. 4, 2013

(65) Prior Publication Data

US 2013/0184726 A1 Jul. 18, 2013

Related U.S. Application Data

(63) Continuation of application No. PCT/EP2011/064923, filed on Aug. 30, 2011.

(30) Foreign Application Priority Data

Sep. 10, 2010 (DE) .......................... 10 2010 037 468

(51) Int. Cl.
| | |
|---|---|
| A61B 17/08 | (2006.01) |
| A61B 17/122 | (2006.01) |
| A61B 17/128 | (2006.01) |
| A61B 17/28 | (2006.01) |
| A61B 17/30 | (2006.01) |
| A61B 19/00 | (2006.01) |

(52) U.S. Cl.
CPC ........... *A61B 17/1227* (2013.01); *A61B 17/128* (2013.01); *A61B 17/2833* (2013.01); *A61B 2017/305* (2013.01); *A61B 2019/304* (2013.01)

(58) Field of Classification Search
CPC ........ A61B 17/122–17/1285; Y10T 24/44274; Y10T 24/44376; Y10T 24/44462; Y10T 24/4447; Y10T 24/44479
USPC .......................... 606/151, 157–158; 294/99.2
See application file for complete search history.

(56) References Cited

U.S. PATENT DOCUMENTS

| | | | |
|---|---|---|---|
| 482,232 A | * | 9/1892 | Delaney ........................ 294/99.2 |
| 884,256 A | | 4/1908 | Addie |

(Continued)

FOREIGN PATENT DOCUMENTS

| | | |
|---|---|---|
| DE | 26 47 018 | 5/1977 |
| DE | 26 58 478 | 4/1978 |

(Continued)

*Primary Examiner* — Todd E Manahan
*Assistant Examiner* — Erich Herbermann
(74) *Attorney, Agent, or Firm* — Lipsitz & McAllister, LLC (57) ABSTRACT

A surgical clip is provided having two clip arms and a resiliently flexible element via which the two clip arms are connected to each other. The two clip arms each have a first free end, these first free ends being held parallel to and in contact with each other with a predetermined closing force by the resiliently flexible element when the clip is in a rest position. The clip arms are held at a second end opposite the free end on the resiliently flexible element. The clip arms have between their first and second ends sections configured to cross each other. The clip arms further have stop elements configured to complement each other. The stop elements are adapted to be brought in mutual contact when the clip is transferred from the rest position to an application position in which the free ends are spaced apart from each other.

17 Claims, 8 Drawing Sheets

(56) References Cited

U.S. PATENT DOCUMENTS

| | | | |
|---|---|---|---|
| 1,589,076 A | 6/1926 | Haskins | |
| 1,758,490 A * | 5/1930 | Aderer | 294/99.2 |
| 1,837,277 A | 12/1931 | Lund | |
| 3,598,125 A | 8/1971 | Cogley | |
| 3,802,437 A | 4/1974 | Kees, Jr. | |
| 3,805,792 A | 4/1974 | Cogley | |
| 3,827,438 A | 8/1974 | Kees, Jr. | |
| 4,192,315 A | 3/1980 | Hilzinger et al. | |
| 4,324,248 A | 4/1982 | Perlin | |
| 4,360,023 A | 11/1982 | Sugita et al. | |
| 4,416,266 A | 11/1983 | Baucom | |
| 4,444,187 A | 4/1984 | Perlin | |
| 4,484,581 A * | 11/1984 | Martin et al. | 606/158 |
| 4,602,631 A | 7/1986 | Funatsu | |
| 4,765,335 A | 8/1988 | Schmidt et al. | |
| 4,777,950 A * | 10/1988 | Kees, Jr. | 606/158 |
| 4,796,625 A | 1/1989 | Kees, Jr. | |
| 4,932,955 A | 6/1990 | Merz et al. | |
| 4,943,298 A * | 7/1990 | Fujita et al. | 606/158 |
| 4,961,743 A | 10/1990 | Kees, Jr. et al. | |
| 4,966,603 A | 10/1990 | Focelle et al. | |
| 4,971,055 A | 11/1990 | von Zeppelin | |
| 4,983,176 A | 1/1991 | Cushman et al. | |
| 5,074,870 A | 12/1991 | von Zeppelin | |
| 5,207,692 A | 5/1993 | Kraus et al. | |
| 5,312,426 A | 5/1994 | Segawa et al. | |
| 5,361,463 A * | 11/1994 | Revis | 24/543 |
| 5,474,569 A | 12/1995 | Zinreich et al. | |
| 5,474,732 A | 12/1995 | Korthoff et al. | |
| 5,520,701 A | 5/1996 | Lerch | |
| 5,924,176 A | 7/1999 | Lee | |
| 5,944,729 A | 8/1999 | Blake | |
| 6,179,850 B1 | 1/2001 | Goradia | |
| 6,210,418 B1 * | 4/2001 | Storz et al. | 606/142 |
| 6,251,117 B1 | 6/2001 | Kringel et al. | |
| 6,457,218 B1 | 10/2002 | Lawrence | |
| 6,537,277 B2 | 3/2003 | Vom Berg et al. | |
| 6,776,783 B1 | 8/2004 | Frantzen et al. | |
| 2002/0022844 A1 | 2/2002 | Vom Berg et al. | |
| 2002/0111643 A1 | 8/2002 | Herrmann et al. | |
| 2002/0117869 A1 * | 8/2002 | Wang et al. | 294/16 |
| 2009/0240266 A1 | 9/2009 | Dennis | |
| 2013/0172914 A1 | 7/2013 | Weisshaupt | |
| 2014/0114332 A1 | 4/2014 | Lutze | |

FOREIGN PATENT DOCUMENTS

| | | |
|---|---|---|
| DE | 29 52 618 | 7/1981 |
| DE | 31 39 488 | 4/1983 |
| DE | 34 19 928 | 4/1985 |
| DE | 35 23 031 | 1/1986 |
| DE | 37 22 311 | 1/1989 |
| DE | 89 11 948 | 1/1990 |
| DE | 43 19 829 | 8/1994 |
| DE | 296 04 518 | 6/1996 |
| DE | 69028200 | 2/1997 |
| DE | 37 23 167 | 4/1997 |
| DE | 297 08 218 | 8/1997 |
| DE | 19737976 | 3/1999 |
| DE | 198 09 121 | 8/1999 |
| DE | 40 00 086 | 5/2000 |
| DE | 19907354 | 9/2000 |
| DE | 10 2006 031 092 | 1/2008 |
| EP | 0 346 084 | 12/1989 |
| EP | 1 196 094 | 1/2003 |
| GB | 1 557 682 | 12/1979 |
| GB | 2 161 206 | 1/1986 |
| WO | WO 99/44511 | 9/1999 |

\* cited by examiner

SURGICAL CLIP

This application is a continuation of international application number PCT/EP2011/064923 filed on Aug. 30, 2011 and claims the benefit of German application number 10 2010 037 468.7 filed on Sep. 10, 2010, which are incorporated herein by reference in their entirety and for all purposes.

BACKGROUND OF THE INVENTION

The invention relates to a surgical clip, in particular for use as an implant, wherein use as an aneurysm clip has outstanding importance here.

Surgical clips are known that have two clip arms and a resiliently flexible element which connects the two clip arms to each other at one of their ends.

The two clip arms each have a first free end, these first free ends being held parallel to and in contact with each other with a predetermined closing force by the resiliently flexible element when the clip is in a rest position, and a second end opposite the free end, these second ends being held on the resiliently flexible element.

Between their first, free end and second end, the clip arms each have sections configured to cross each other. The clip can be transferred from the rest position to an application position by the second ends being gripped with a tool, in particular a clip application forceps, and approximated to each other against the spring force of the resiliently flexible element.

An essential parameter of the surgical clips is their closing force: it must be precisely set and also, in particular if the surgical clip is used as an implant, be maintained on a permanent basis.

Therefore, the surgical clips of the kind mentioned at the outset are precisely set as to their closing force in an elaborate process and require high precision with tolerances that are partly in the range of a hundredth of a millimeter. Only in this way can a reproducible closing pattern of the clips be achieved.

In order not to stress the resiliently flexible element beyond the elastic range when applying the clips, clip application forceps that are suited to the different clips are provided, said clip application forceps being configured such that overstretching the clip and thus deforming the clip beyond the elastic range cannot occur. This can be accomplished for example by limiting the closing angle of the forceps. Different clips require clip application forceps specifically adapted for those clips.

With the clips of different closing force requiring differently configured clip application forceps, there is the danger of the application forceps being accidentally interchanged, with the risk of a clip being opened too far and the resiliently flexible element undergoing plastic deformation. This would reduce the designated closing force of the clip, and this may pose a great danger to the patient in whom such an implant has been implanted.

It is an object of the present invention to provide a surgical clip which is easy to handle and is nonetheless safely useable as an implant.

SUMMARY OF THE INVENTION

In accordance with the invention, this object is accomplished by a surgical clip having the features of claim 1.

The stop elements formed complementary to each other on the clip arms make it possible to ensure that regardless of whether or not a suitable application forceps is used for applying the clip, the latter is not opened beyond its maximum admissible opening and the resiliently flexible element is stressed at most to its maximum admissible elastic deformation.

Preferably, the stop elements are arranged in line with a force application plane in which the forces of the clip application forceps act when the clip is transferred from the rest position to the application position.

This eliminates the possibility of tilting moments resulting when the stop elements are in contact with each other.

More preferably, the complementary-configured stop elements are configured such that guiding the clip arms in a lateral direction results when transferred to the application position. This further ensures that the clip arms reach the application position in the plane predetermined for them and, as long as the forces of the clip application forceps act, also remain within that plane and cannot deflect laterally.

A preferred example of the complementary configuration of the stop elements is a prism structure in which the edges of the prism are oriented parallel to the longitudinal direction of the clip arms. Preferably, one clip arm is formed with a positive prism structure, whereas the other stop element has the negative structure complementary thereto.

In a variant of simpler design, a prism structure of negative configuration can receive and sufficiently centre the already existing, outward-curved structure of the second end of the other clip arm. Further, the prism structure need not necessarily have its outermost region formed by a sharp prism edge. Rather, the outermost region can also be shaped in a flattened or rounded configuration without impairing the function of the stop element.

In a more preferred embodiment, the complementary-configured stop elements are configured such that axial guiding of the clip arms results when transferred to the application position. This prevents the clip arms, in particular the free ends thereof as viewed in the longitudinal direction, from being displaced relative to each other under the action of force.

Particularly preferred complementary-configured stop elements are those which effect both lateral and axial guiding of the clip arms. Particularly preferred examples of such complementary-configured stop elements are ball, cone or pyramidal structures, and these may also include truncated cone or truncated pyramid shapes.

In a preferred embodiment of the surgical clips in accordance with the invention, it is provided for one of the clip arms to be formed in the crossing region thereof with an elongated opening therethrough extending in a longitudinal direction of the clip arm, with the other clip arm then being arranged to be guided with its crossing region within the elongated opening.

In particular, this embodiment ensures that the orientation of the free ends of two clip arms is additionally secured and that unintentional deflecting movement of the clip arms cannot result, not even under the action of a considerable force exerted by the clip application forceps (for corresponding closing forces of the clip).

In embodiments using an elongated opening, the stop elements can be implemented in a simple manner by calibrating the elongated opening and/or the section of the other clip arm that is guided within the elongated opening.

The elongated opening can be configured as a through-opening within a clip arm. Alternatively, it is possible for a longitudinal element to be fixed, in particular welded, in parallel to a section of the clip arm and keeping a distance from the clip arm, to thus form the elongated opening.

Preferably, the section of the clip arm to which the longitudinal element is fixed in parallel is formed with a reduced cross-section, in particular a flattened cross-section, with the flattened part of the clip arm forming part of the elongated opening.

Preferably, the longitudinal element is configured as a sheet element having one surface thereof arranged parallel to the flattening of the section of the clip arm. Optionally, the sheet element can comprise an angled section that partially overlies the elongated opening which is formed between the longitudinal element and the section of the clip arm. This is an easy way of providing the longitudinal element with the function of a stop element. In particular, an edge of the angled region of the sheet element can form a stop element for the other clip arm.

In preferred embodiments of the surgical clips constructed in accordance with the invention, the stop elements are arranged in the section of the second ends of the clip arms.

In an alternative preferred embodiment, the stop elements can be arranged in the section of the crossing regions, particularly in embodiments comprising an elongated opening in the area of the crossing regions.

The resiliently flexible element of the surgical clips constructed in accordance with the invention can be configured in different ways. In accordance with a preferred variant of the surgical clips constructed in accordance with the invention, the resiliently flexible element comprises a semi-circular spring coil.

More preferably, the resiliently flexible element has a spring coil of one-and-a-half turns.

For the purpose of precisely positioning a clip application tool, provision may be made for the surgical clips constructed in accordance with the invention to have at the exterior surfaces of the clip arms in the area of the second ends thereof positioning elements for the tool, in particular for a clip application forceps.

The positioning elements may be configured in a variety of ways; particularly preferred positioning elements are those that are configured as a depression or outward-protruding pins.

It is particularly preferred for the positioning elements to be arranged in alignment with the stop elements so that the positioning elements, which at the same time define the area of contact between the clip and the clip application forceps, cause the force applied by the clip application forceps to be applied in the area of the stop elements, thus allowing particularly safe limitation of the forces acting on the resiliently flexible element.

As has already been mentioned at the outset, the surgical clip constructed in accordance with the invention is in particular configured as an aneurysm clip, in particular also as a cerebral aneurysm clip.

These and further advantages of the invention are described in more detail below with reference to the drawing.

DETAILED DESCRIPTION OF THE INVENTION

Figure 1:
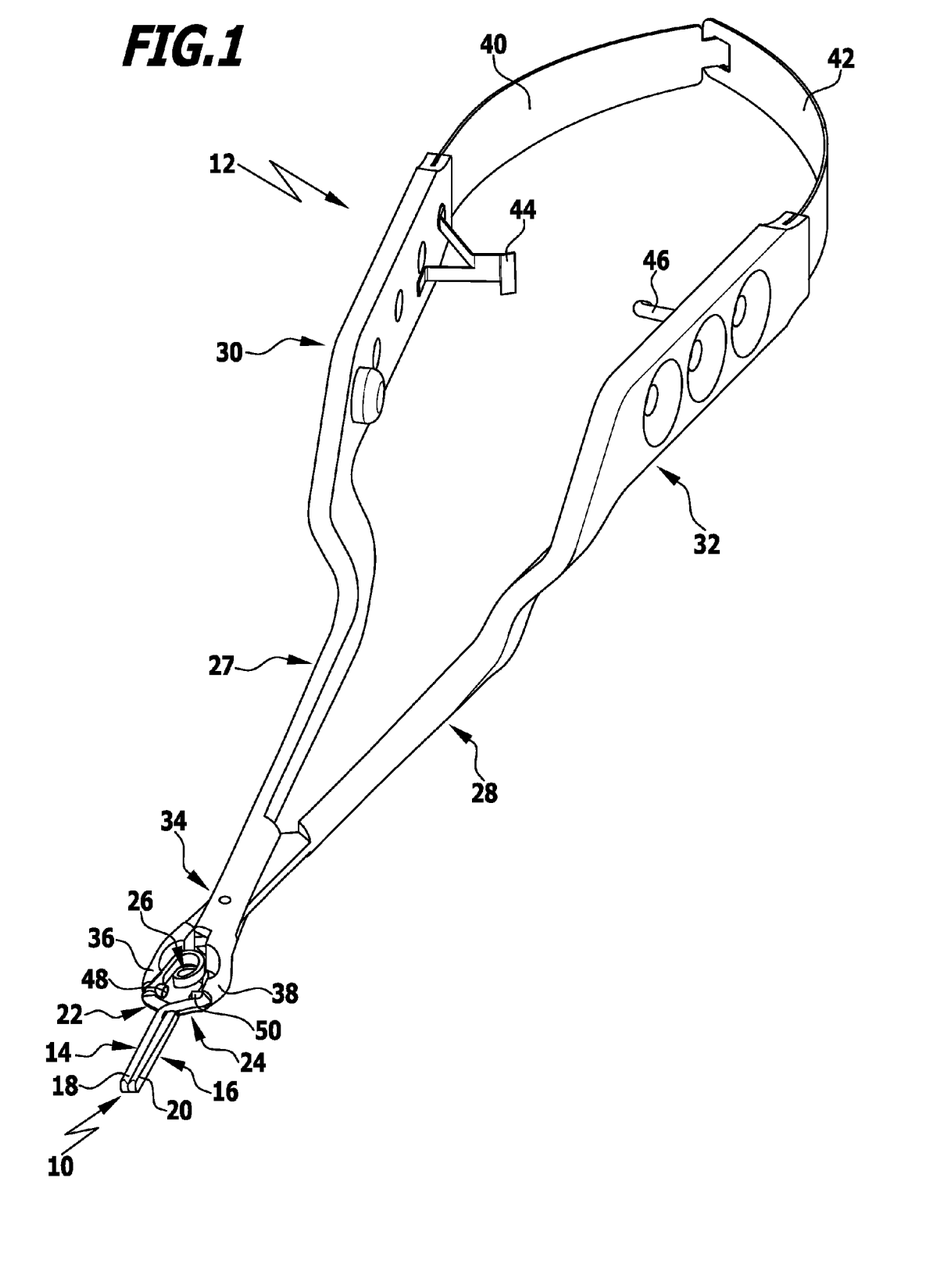
FIG. 1 shows an aneurysm clip in accordance with the invention held by a clip application forceps.

FIG. 1 shows a surgical clip 10 constructed in accordance with the invention, with the surgical clip being held in a clip application forceps 12.

The surgical clip 10 constructed in accordance with the invention, which will be described in greater detail in conjunction with FIG. 2, comprises two clip arms 14, 16, the first free ends 18, 20 of which are in surface contact with each other when the clip is in closed condition, i.e., in its rest position, as shown in FIG. 1.

The two clip arms 14, 16 are configured to cross each other and their second ends 22, 24 opposite the first free ends 18, 20 are connected to each other via a spring element 26.

The clip application forceps 12 has two handle arms 27, 28 which are adjoined by two handle parts 30, 32. The handle arms 27, 28 are articulately interconnected at their front region 34.

The jaw parts 36, 38 of the forceps 12, which adjoin the handle arms 27, 28 beyond the articulation 34, are formed with concave structures oriented toward each other so that they can securely receive the second ends 22, 24 of the clip arms, which are connected to the spring element 26.

Arranged on the opposite end of the handle parts 30, 32 are two leaf springs 40, 42 which are articulately connected to each other at their free ends so that the clip application forceps, in the non-actuated condition, does not exert any pressure on the clip 10 and can be released from the clip 10 without force.

In order to apply the surgical clip 10 constructed in accordance with the invention, the handle parts 30, 32 are urged toward each other and, if required, retained in this condition by way of locking elements 44, 46. In this condition, the jaw parts 36, 38 urge the second ends 22, 24 of the clip arms 14, 16 toward each other, thereby opening the free ends 18, 20 of the clip to the latter's application position.

The maximum opening angle of the free ends 18, 20, i.e., the application position, is determined by stop elements 48, 50. In this way, the opening angle of the clip 10 constructed in accordance with the invention is limited, ensuring that the spring element 26 is deformed only within the elastic range and that the designated closing force of the clip is maintained after the application thereof.

Figure 2:
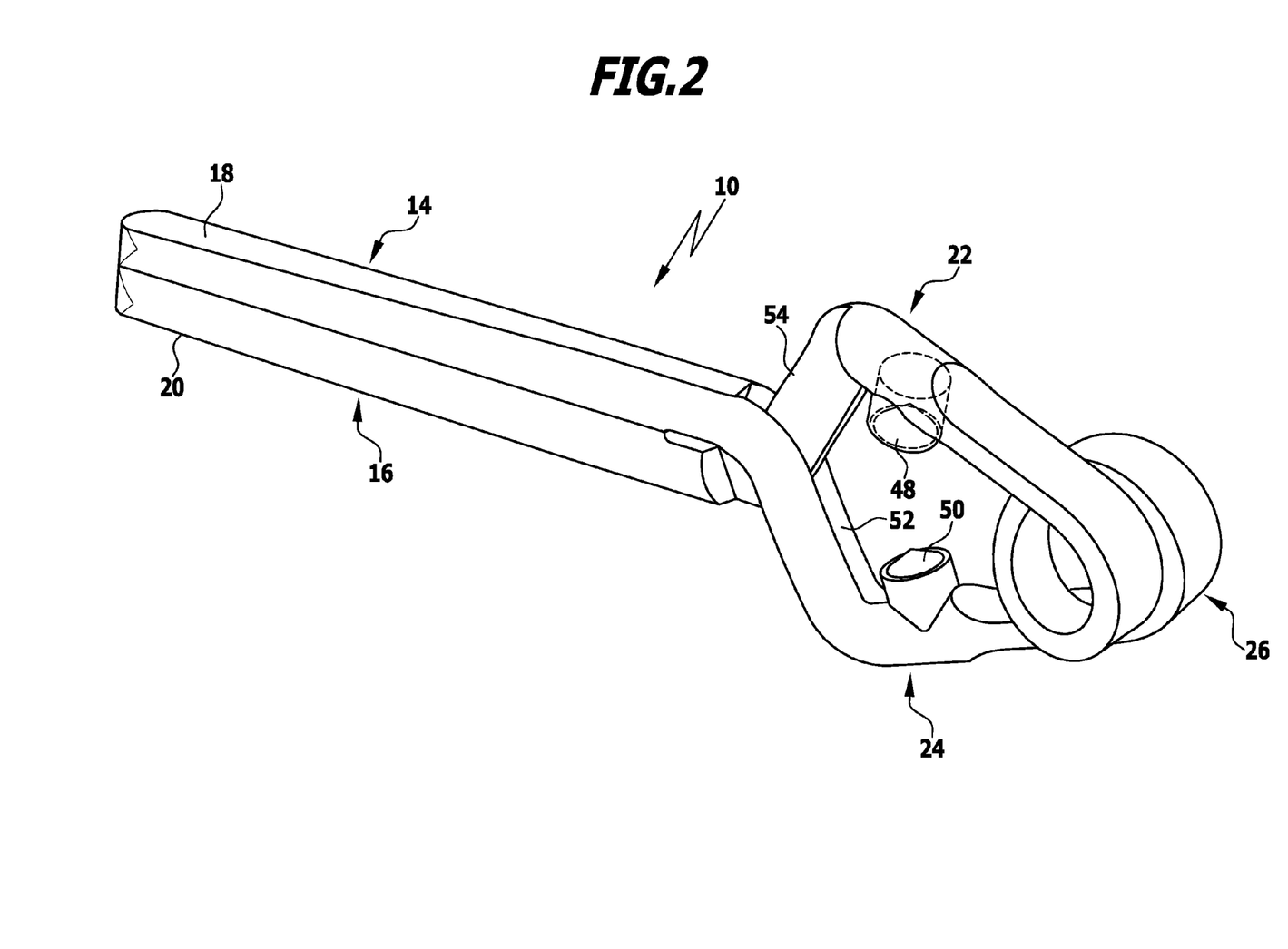
FIG. 2 shows an enlarged view of the aneurysm clip of FIG. 1.

FIG. 2 shows in detail the surgical clip 10 from FIG. 1, constructed in accordance with the invention, with the surgical clip illustrated in the rest position, i.e., with the two first free ends 18, 20 of the two clip arms 14, 16 arranged parallel to and in contact with each other.

The two clip arms 14 and 16 are connected to each other by way of the resiliently flexible element 26, which comprises a 1.5-turn spring coil.

The seconds ends 22, 24 of the two clip arms 14, 16 comprise in each case an inward-directed stop element 48, 50, the stop element 48 having a cone-shaped depression and the stop element 50 having a correspondingly formed elevation in the shape of a cone.

When the two seconds ends 22, 24 of the two clip arms 16, 14 are urged toward each other, the cone-shaped elevation of the stop element 50, in the maximum opened condition (application position) of the free ends 18, 20, engages in the cone-shaped recess of the stop element 48, preventing further opening of the surgical clip 10.

This ensures that the resiliently flexible element 26 is deformed only within its elastic range, thus avoiding the plastic range and maintaining for the clip the closing force that has been precisely set before, in the process of manufacture.

The areas of the clip arms 14, 16 between the free ends 18, 20 and the seconds ends 22, 24 are configured to cross each other such that the arm 18 has an opening 52 extending in a longitudinal direction of the arm, a corresponding flattened section 54 of the clip arm 16 being guided therethrough. Guiding the clip arm 16 in the area of its section 54 within the longitudinal opening 52 of the clip arm 14 already ensures that the orientation of the two free ends 18 and 20 relative to each other is maintained substantially throughout the action during which the free ends 18, 20 are transferred from the rest position, as shown in FIG. 2, to an application position.

On the one hand, the stop elements 48, 50 provide for the opening of the clip not to be continued beyond the maximum admissible opening position (application position); on the other hand, the cone-shaped projection of the stop element 50 in cooperation with the cone-like recess of the stop element 48 additionally achieves exact centring of the second ends 22, 24 and thus exact orientation of the free ends 18, 20 in the application position which is effective both in a lateral and in a longitudinal direction.

This result is obtained independent of whether or not clip application forceps specifically suited to the clip 10 are used.

Figure 3:
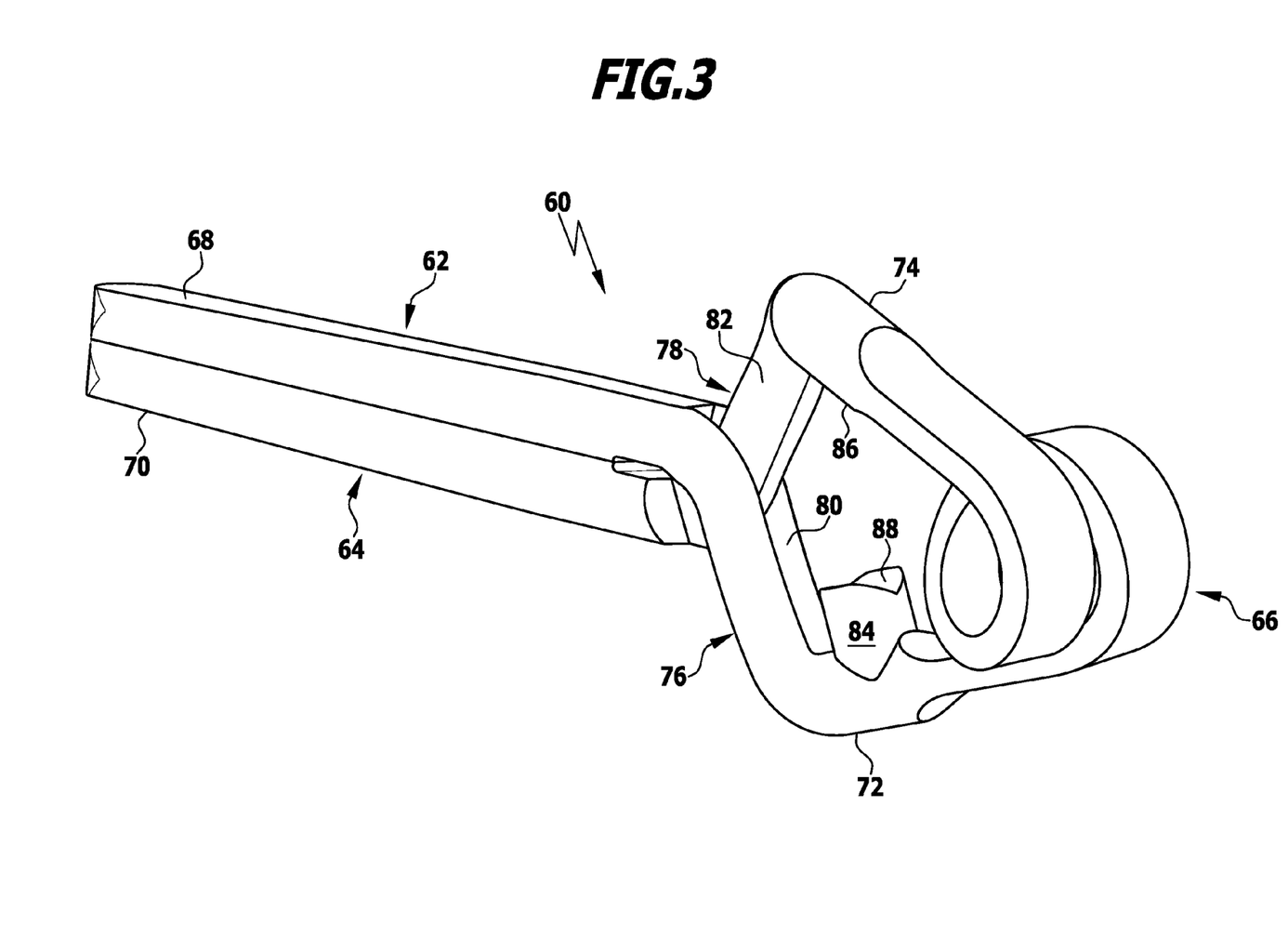
FIG. 3 shows an alternative embodiment of a clip constructed in accordance with the invention.

FIG. 3 shows another embodiment of a surgical clip 60 in accordance with the invention having two clip arms 62, 64 which are connected to each other via a resiliently flexible element 66. Again, the resiliently flexible element 66 has been precisely set to a predetermined closure force of the clip 60 during production of the clip 60.

In the closed position (rest position) of the clip 60, shown in FIG. 3, two first free ends 68, 70 of the clip arms 62, 64 are in surface contact with each other.

The second ends 72, 74 of the two clip arms 62, 64 opposite the free ends 68, 70 thereof are connected to the spring element 66. The middle regions 76, 78 of the two clip arms 62, 64 respectively, located between the respective ends 68, 72 and 70, 74 respectively, are configured to cross each other, with the middle region 76 of the one clip arm 62 having an elongated opening or elongated hole 80 within which a flattened part 82 of the middle region 78 of the other clip arm 64 is guided.

At its two ends 72, 74, the clip 60 has stop elements 84, 86, of which the stop element 84 extends in the shape of a pin in a direction toward the second end 74 of the arm 64.

The stop element 86 of the arm 64 is formed by the surface of the substantially cylindrically shaped second end 74 of the arm 64.

For receiving and centring in a lateral direction, the stop element 84 has a prism-shaped or wedge-shaped depression 88 in which the cylindrical surface 86 of the second end 74 of the clip arm 64 engages and is thereby centred.

The resiliently flexible element 66 of the clip 60 has a 1.5-turn spring coil.

As an alternative to the surface 86 of the cylindrical end 74, provision could also be made for a pin-shaped projection corresponding to the stop element 84 and pointing in a direction toward the second end 72 of the clip arm 62 to be provided in lieu of the surface 86, said projection then being preferably provided with a prism-shaped protruding cross-section which is configured complementary to the recess 88 and allows the lateral orientation of the two ends 72, 74 in the application position to be even more precise.

Figure 4:
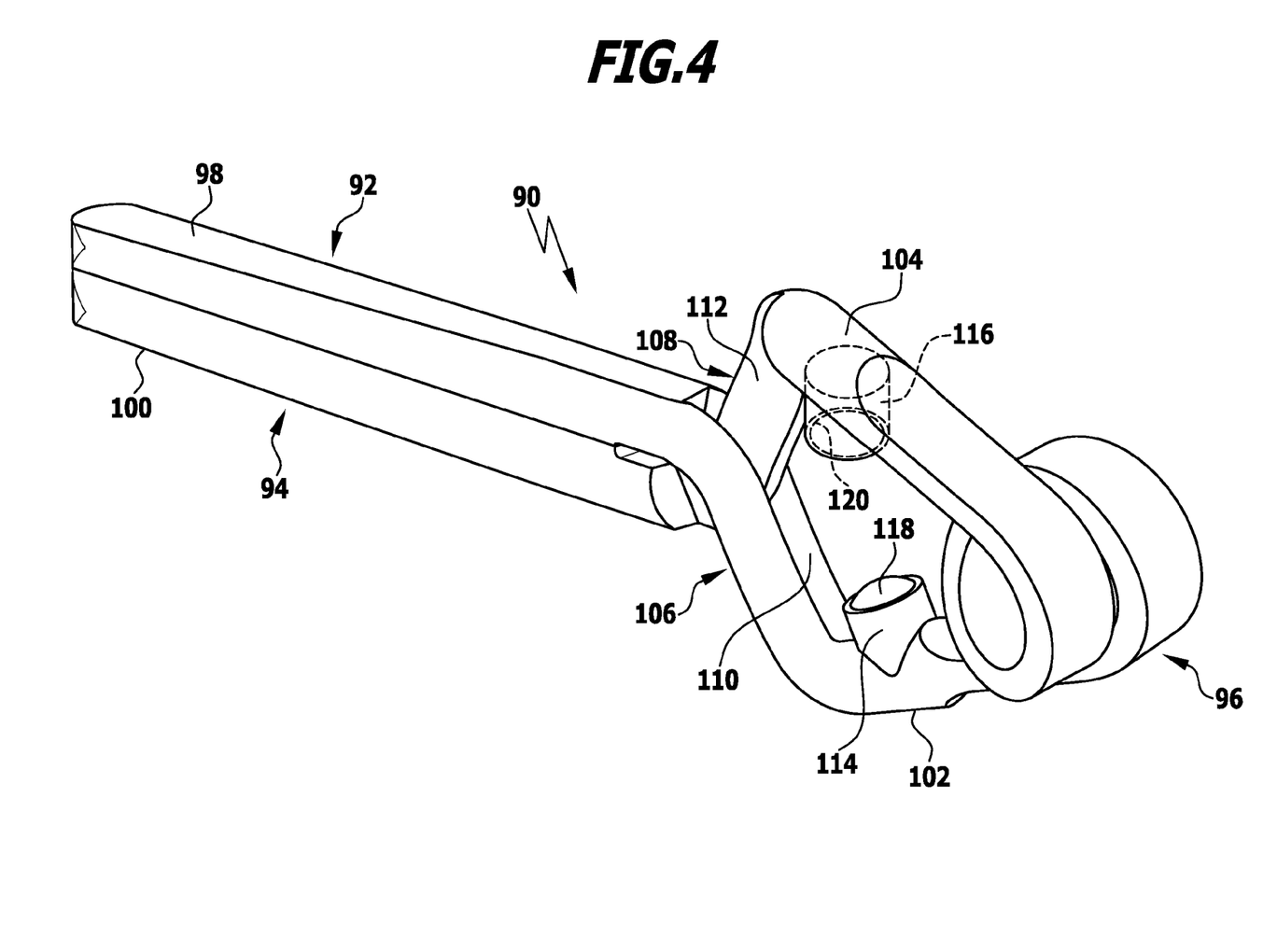
FIG. 4 shows a further embodiment of a clip constructed in accordance with the invention.

FIG. 4 shows a surgical clip 90 constructed in accordance with the invention, again illustrated in a closed position (rest position) in which the two first free ends 98, 100 of the clip arms 92, 94 are in contact with each other.

The second ends 102, 104 of the two clip arms 92, 94 opposite the free ends 98, 100 thereof are connected to a spring element 96. The middle regions 106, 108 of the two clip arms 92, 94 respectively, located between the respective ends 98, 100 and 102, 104 respectively, are configured to cross each other, with the middle region 106 of the clip arm 92 having an elongated opening or elongated hole 110 within which a flattened part 112 of the middle region 108 of the clip arm 94 is guided.

At its two ends 102, 104, the clip 90 has stop elements 114, 116, of which the stop element 114 extends in the shape of a pin in a direction toward the second end 104 of the arm 94 and terminates in a spherical section 118.

The stop element 116 of the arm 94 is likewise formed by a pin-shaped projection, the end thereof facing toward the stop element 114 having a spherical shell shaped recess 120 formed thereon.

The resiliently flexible element 96 of the clip 90 has a 1.5-turn spring coil.

FIGS. 5A to 5C illustrate again, in schematic form and by reference to a further embodiment of a surgical clip 140 constructed in accordance with the invention, the handling of the clip in conjunction with a clip applying forceps 142, which is only partially shown.

Figure 5A:
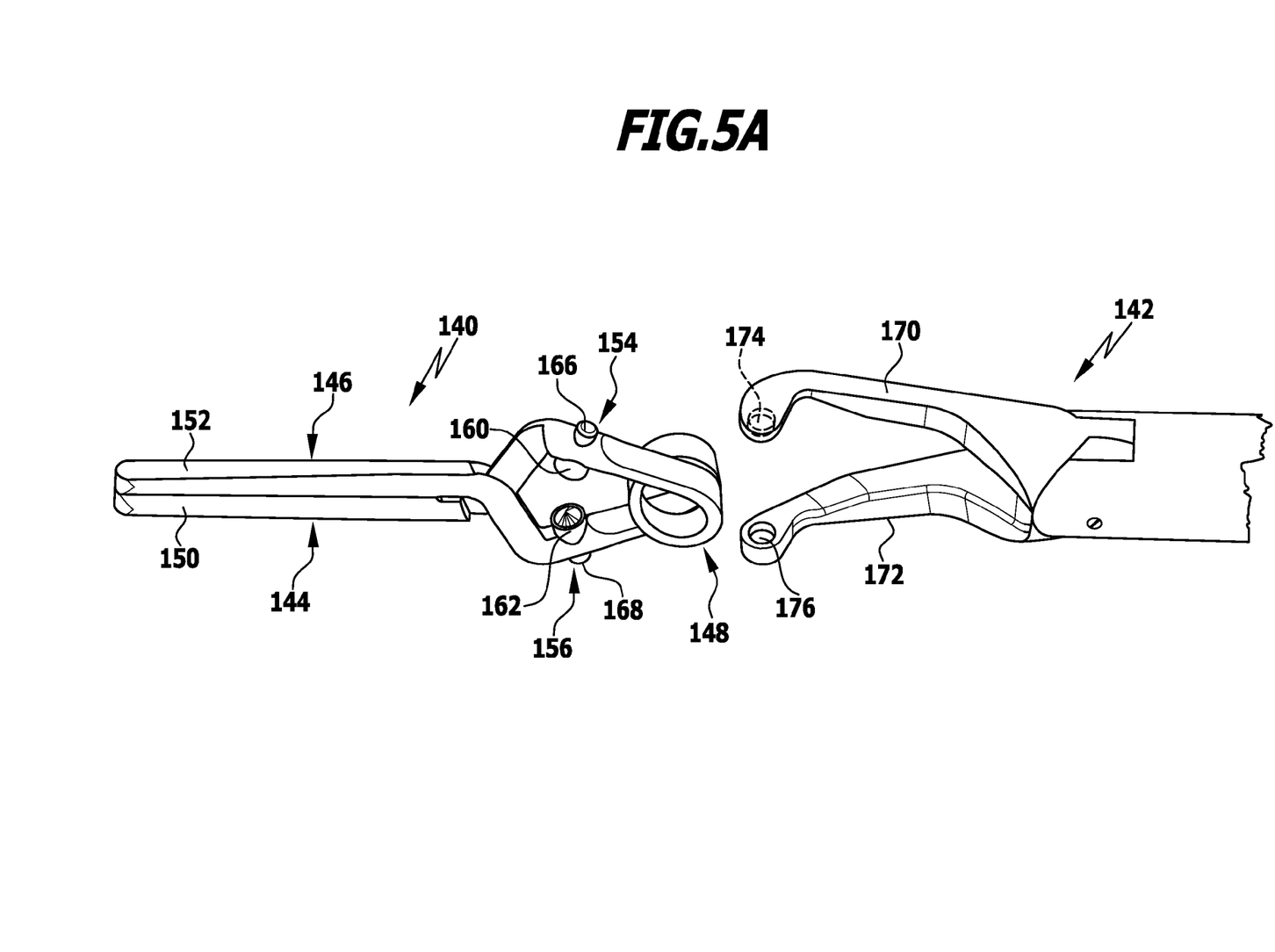
FIGS. 5A to 5C show a further embodiment of a clip constructed in accordance with the invention in different positions in relation to and in association with a clip application forceps.
Figure 5B:
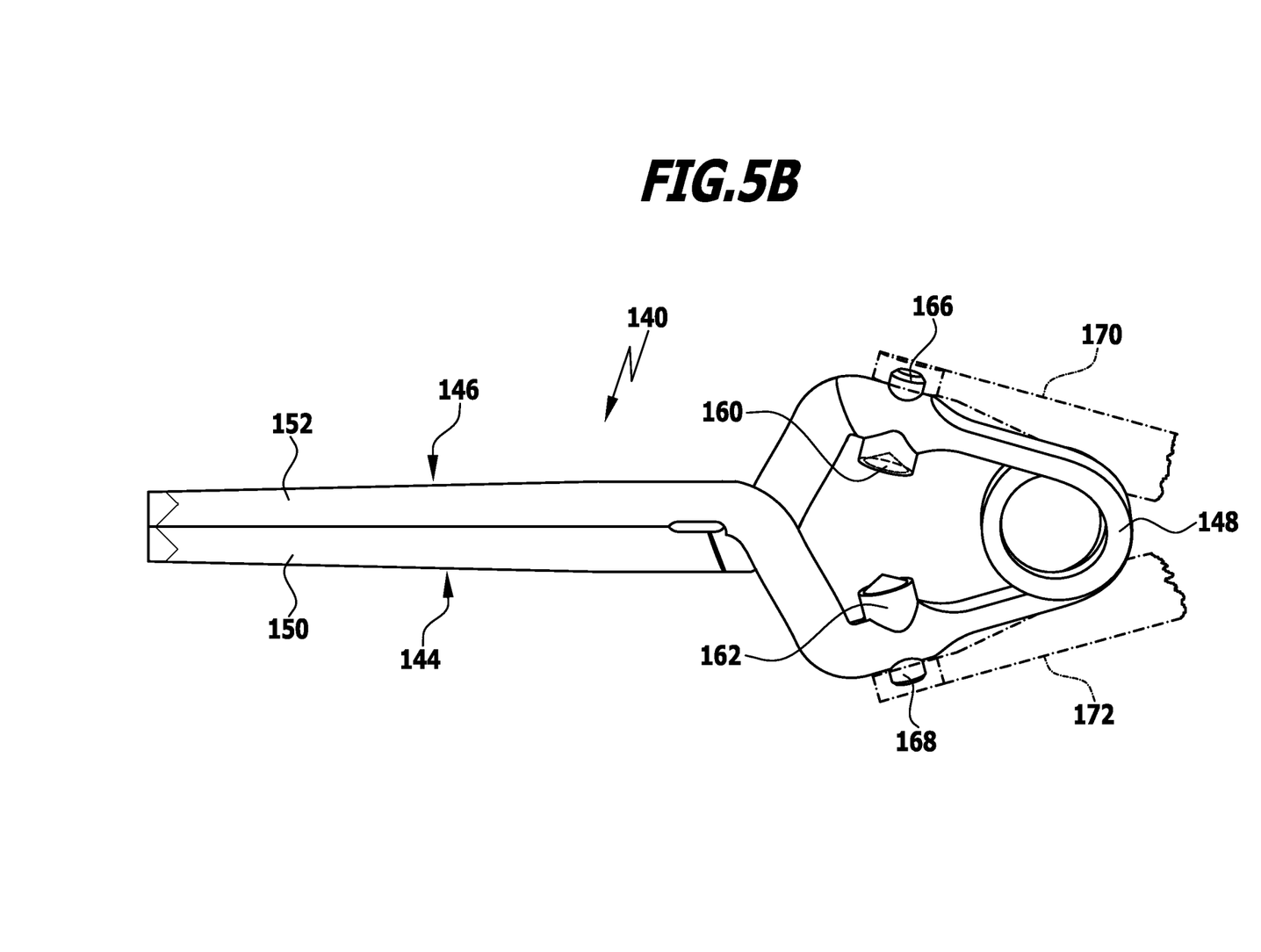
Figure 5C:
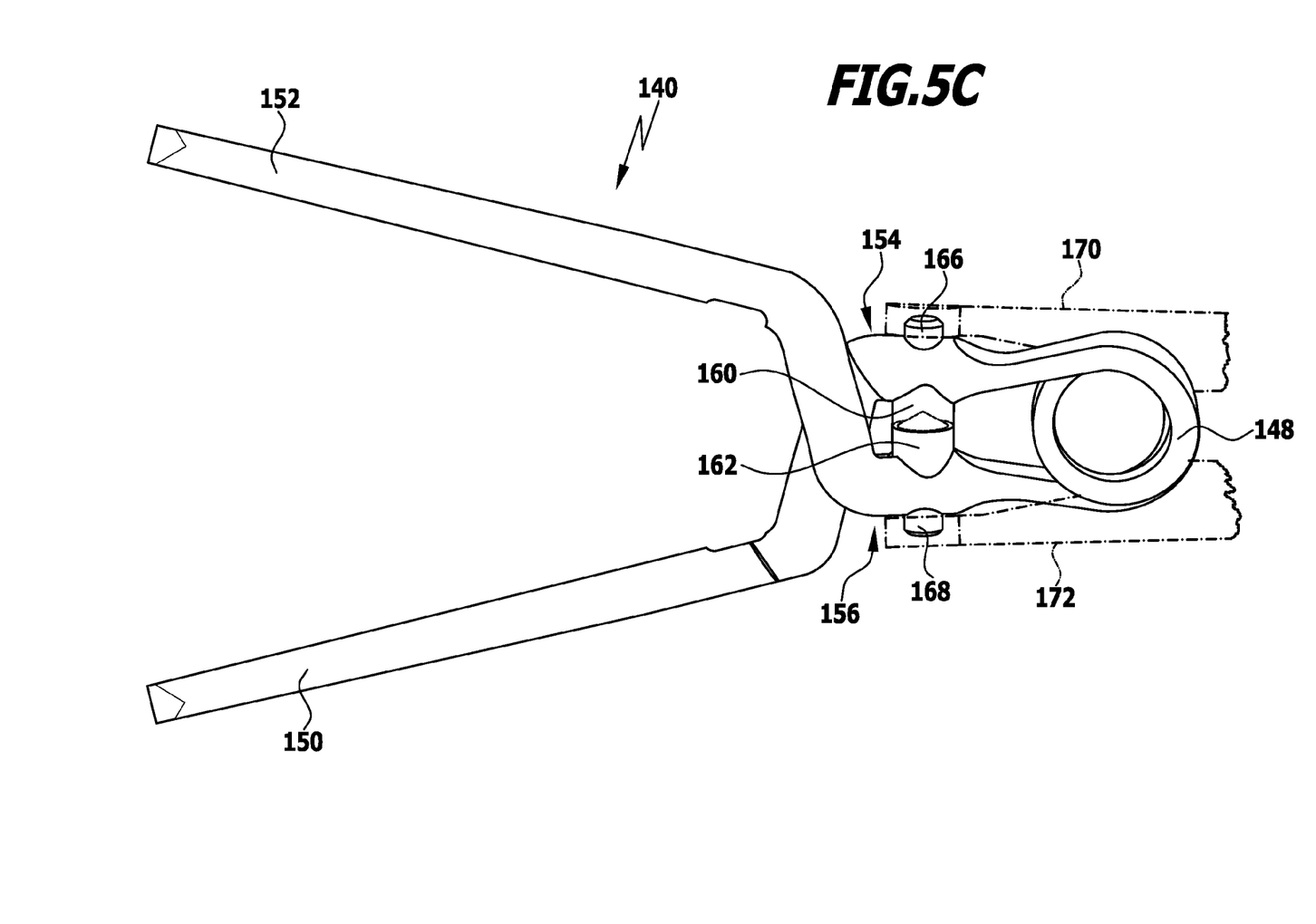

The clip 140 has two clip arms 144, 146, the first free ends 150, 152 of which are parallel to and in contact with each other when in the rest position and the second ends 154, 156 of which are connected to each other via a resiliently flexible element 148.

The configuration of the clip 140 constructed in accordance with the invention substantially corresponds to that of the clip 10, which is shown in FIG. 2, so that reference may generally be made to the explanations given there.

Arranged in the area between the ends 150, 154 and 152, 156 are mutually crossing middle regions of the two clip arms 144, 146 respectively, which are configured in the same way as shown and described in FIG. 2 for clip 10.

The clip 140 also has stop elements 160, 162 which comprise a cone-shaped recess (in the stop element 160; not shown) and a cone-shaped projection on the stop element 162.

Now, in addition to the characteristics of the surgical clip 10 of FIG. 2, the surgical clip 140 of FIGS. 5A to 5C has cylindrical projections 166, 168 which project outwardly from the second ends 154, 156 and which, when handling the clip 140, serve the secure connection thereof to the clip applying forceps 142 and in particular the exact placement of the clip 140 between jaw parts 170, 172 of the clip applying forceps 142. To this end, the two jaw parts 170, 172 have at the free ends thereof depressions 174, 176 which are configured complementary to the pin-shaped projections 166, 168 of the clip 140 and receive and centre these.

As shown in FIG. 5A, the jaw parts 170, 172 of the clip applying forceps 142 can be shaped in an offset configuration in order to thus grip the clip 140 in a lateral position.

FIG. 5B shows the situation of the clip 140 in a rest position in which the two jaw parts 170, 172, via the two pins 166, 168, have already been centred and docked with the openings 174, 176 provided in the jaw part ends.

FIG. 5B shows the two free ends 150, 152 of the clip arms 144, 146 as still being in the rest position.

FIG. 5C shows the situation when the ends 154, 156, by the clip applying forceps 142 or the jaw parts 170, 172 thereof, are urged together until the two stop elements 160, 162 come into engagement and into contact with each other, the clip 140 thus being transferred to the application position. The jaw parts 170, 172 of the clip applying forceps 142, via the pin-shaped projections 166, 168, remain centred and fixed at the correct position of the clip 140, and—as shown in FIG. 5C—the forces applied across the areas adjacent to the pin-shaped projections 166, 168 are substantially linearly absorbed via the stop elements 160, 162.

Figure 6:
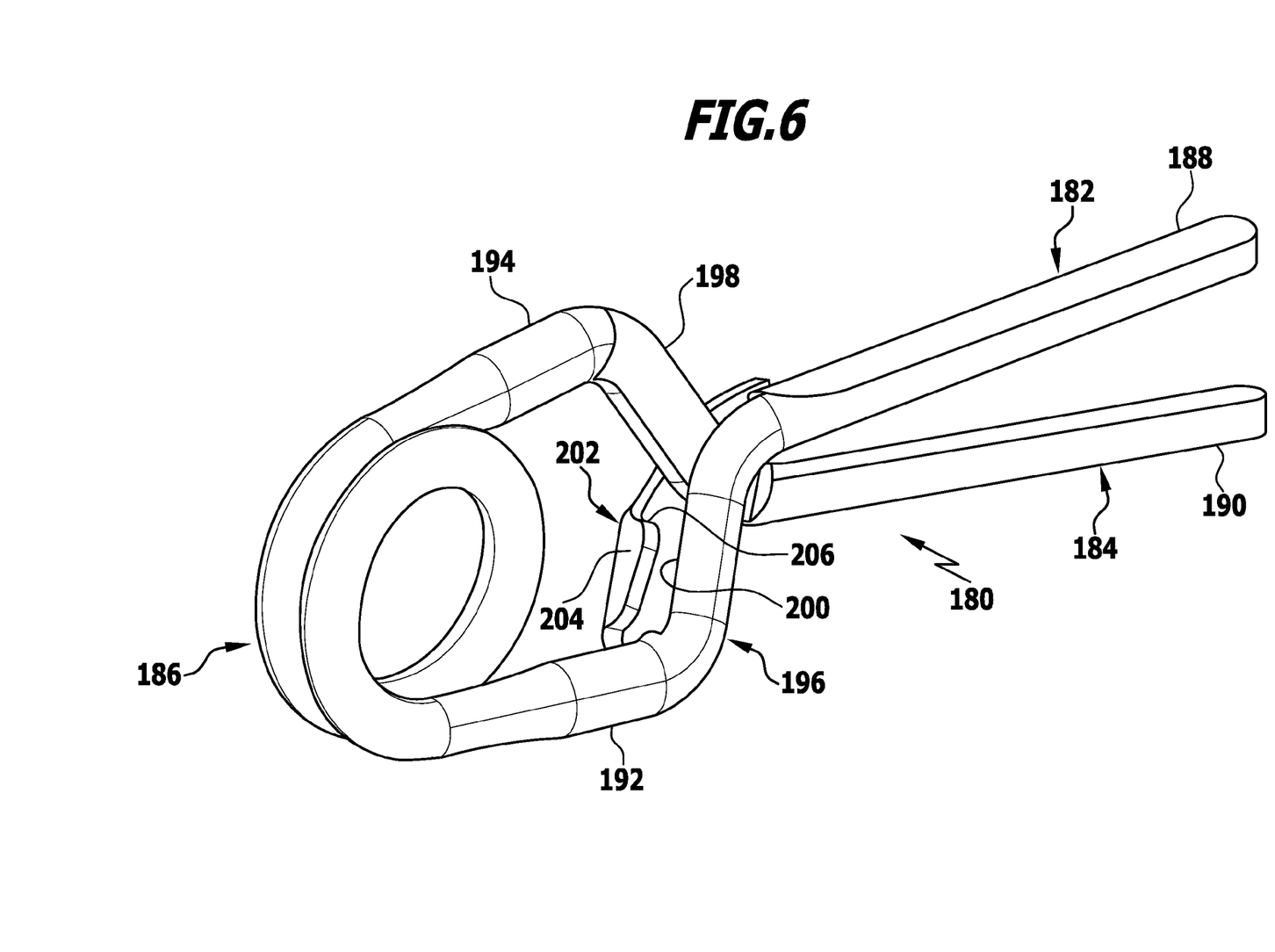
FIG. 6 shows another embodiment of a clip constructed in accordance with the invention.

FIG. 6 shows another embodiment of a surgical clip 180 constructed in accordance with the invention, with the clip depicted in a position between the rest position and the application position, i.e., partially opened.

The clip 180 constructed in accordance with the invention has two clip arms 182, 184 which are connected to each other by way of a resiliently flexible element 186 which comprises a 1.5-turn spring coil. The resiliently flexible element 186 has been precisely set to a predetermined closure force of the clip in the process of producing the clip.

The two first free ends 188, 190 of the clip arms 182, 184 are shown slightly spaced apart from each other, corresponding to the slightly opened position of the clip 180.

The second ends 192, 194 of the two clip arms 182, 184 opposite the free ends 188, 190 thereof are connected directly to the spring element 186. The sections 196, 198 of the two clip arms 182, 184 respectively, located between the respective ends 188, 192 and 190, 194 respectively, are configured to cross each other, with the middle region 196 of the one clip arm 182 having a recessed region 200 on which a flattened part of the middle section 198 of the other clip arm 184 is guided.

The recessed region 200 of the middle section 196 of the clip arm 182 is bridged by a longitudinal element 202 which is connected, for example welded, at each of the two ends thereof to the middle section 196 of the clip arm 182. The longitudinal element 202 together with the recessed region 200 of the middle section 196 of the clip arm 182 thus forms an elongated opening in which the flattened part of the middle section 198 of the clip arm 184 is then guided.

Preferably, the longitudinal element 202 is formed from a sheet material, wherein more preferably, the longitudinal element 202 has a projection 204 directed in the direction of the elongated opening, with said projection 204 here being formed in a simple way by bending the sheet material of the longitudinal element 202.

The edge 206 of the longitudinal element 202 pointing upward in FIG. 6 at the same time serves as a stop element which together with the complementary underside of the middle section 198 of the clip arm 184 as an additional stop element limits the maximum opening of the clip 180 and thus the maximum elastic deformation of the spring element 186.

The invention claimed is:

1. Surgical clip for use as an implant, comprising:
two clip arms, and
a resiliently flexible element via which the two clip arms are connected to each other,
the two clip arms each having a first free end, the first free ends being held parallel to and in contact with each other with a predetermined closing force by the resiliently flexible element when the clip is in a rest position,
the clip arms each being held at a second end thereof opposite the free end on the resiliently flexible element, and
the clip arms having between the free end and the second end, sections configured to cross each other,
the clip arms having stop elements configured to complement each other, said stop elements being adapted to be brought into direct mutual contact with each other when the clip is transferred from the rest position to an application position in which the free ends of the clip arms are spaced apart from each other,
wherein:
the complementary-configured stop elements are arranged in line with a force application plane in which the transfer of the clip from the rest position to the application position is carried out; and
the complementary-configured stop elements are configured such that axial alignment of the clip arms results when the clip is transferred to the application position.

2. Surgical clip in accordance with claim 1, wherein the complementary-configured stop elements are configured such that lateral guiding of the clip arms results when the clip is transferred to the application position.

3. Surgical clip in accordance with claim 2, wherein the complementary-configured stop elements comprise one of a wedge structure or a prism structure.

4. Surgical clip in accordance with claim 1, wherein the complementary-configured stop elements are configured such that lateral and axial guiding results when the clip arms are transferred from the rest position to the application position.

5. Surgical clip in accordance with claim 4, wherein the complementary-configured stop elements comprise one of a ball structure, a cone structure or a pyramidal structure.

6. Surgical clip in accordance with claim 1, wherein:
one of the clip arms is formed, in the section configured to cross the other clip arm, with an elongated opening therethrough extending in a longitudinal direction of the clip arm and the other section of the other clip arm is arranged to be guided within the elongated opening.

7. Surgical clip in accordance with claim 6, wherein the elongated opening is formed in a section of one of the clip arms which has an area of reduced cross-section, together with a longitudinal element fixed thereto in parallel.

8. Surgical clip in accordance with claim 7, wherein:
the longitudinal element is a sheet element and comprises an angled section that partially overlies the elongated opening,
the longitudinal element, at the angled section thereof, forms the stop element of the clip arm.

9. Surgical clip in accordance with claim 6, wherein the stop elements are arranged in the elongated opening of the one clip arm and on the section of the other clip arm that is guided within the elongated opening.

10. Surgical clip in accordance with claim 1, wherein the stop elements are arranged in a section of the second ends of the clip arms.

11. Surgical clip in accordance with claim 1, wherein the stop elements are arranged in the sections of the clip arms which are configured to cross each other.

12. Surgical clip in accordance with claim 1, wherein the resiliently flexible element comprises one of a semi-circular spring coil or a spring coil of one-and-a-half turns.

13. Surgical clip in accordance with claim 1, wherein the clip arms have at exterior surfaces in an area of the second ends positioning elements for a tool.

14. Surgical clip in accordance with claim 13, wherein the positioning elements are arranged in alignment with the stop elements.

15. Surgical clip in accordance with claim 13, wherein the positioning elements are configured as one of a depression or outward-protruding pins.

16. Surgical clip in accordance with claim 1, wherein the clip is configured as an aneurysm clip.

17. Surgical clip for use as an implant, comprising:
two clip arms, and a resiliently flexible element via which the two clip arms are connected to each other, the two clip arms each having a first free end, the first free ends being held parallel to and in contact with each other with a predetermined closing force by the resiliently flexible element when the clip is in a rest position, the clip arms each being held at a second end thereof opposite the free end on the resiliently flexible element, and the clip arms having between the free end and the second end, sections configured to cross each other, the clip arms having stop elements configured to complement each other, said stop elements being adapted to be brought into direct mutual contact with each other when the clip is transferred from the rest position to an application position in which the free ends of the clip arms are spaced apart from each other, wherein:

the complementary-configured stop elements are arranged in line with a force application plane in which the transfer of the clip from the rest position to the application position is carried out; and the stop elements are arranged in the sections of the clip arms which are configured to cross each other.

* * * * *